US010478812B2

(12) United States Patent
Eisenschmid et al.

(10) Patent No.: US 10,478,812 B2
(45) Date of Patent: Nov. 19, 2019

(54) METHODS TO STORE TRANSITION METAL ORGANOPHOSPHOROUS LIGAND BASED CATALYSTS

(75) Inventors: Thomas C. Eisenschmid, Cross Lanes, WV (US); Michael C. Becker, League City, TX (US); Donald L. Campbell, Jr., Sorrento, LA (US); Michael A. Brammer, Lake Jackson, TX (US); Glenn A. Miller, South Charleston, WV (US); Edward Adrian Lord, London (GB); Jens Rudolph, Worms (DE); Hans-Rüdiger Reeh, Einselthum (DE)

(73) Assignees: Dow Technology Investments LLC, Midland, MI (US); BASF SE, Ludwigshafen (DE)

( * ) Notice: Subject to any disclaimer, the term of this patent is extended or adjusted under 35 U.S.C. 154(b) by 1135 days.

(21) Appl. No.: 14/111,919

(22) PCT Filed: Apr. 13, 2012

(86) PCT No.: PCT/US2012/033528
§ 371 (c)(1),
(2), (4) Date: Oct. 15, 2013

(87) PCT Pub. No.: WO2012/145241
PCT Pub. Date: Oct. 26, 2012

(65) Prior Publication Data
US 2014/0051568 A1 Feb. 20, 2014

Related U.S. Application Data

(60) Provisional application No. 61/476,593, filed on Apr. 18, 2011.

(51) Int. Cl.
C07C 45/50 (2006.01)
C07C 45/49 (2006.01)
B01J 31/02 (2006.01)
B01J 31/18 (2006.01)
C07F 9/572 (2006.01)

(52) U.S. Cl.
CPC ......... B01J 31/0255 (2013.01); B01J 31/185 (2013.01); B01J 31/186 (2013.01); C07F 9/572 (2013.01); C07F 9/5728 (2013.01); B01J 2231/321 (2013.01); B01J 2531/822 (2013.01); Y02P 20/582 (2015.11)

(58) Field of Classification Search
None
See application file for complete search history.

(56) References Cited

U.S. PATENT DOCUMENTS 3,527,809 A 9/1970 Pruett et al.
4,148,830 A 4/1979 Pruett et al.
4,169,861 A 10/1979 Hughes
4,247,486 A 1/1981 Brewester et al.
4,567,306 A 1/1986 Dennis et al.
4,593,127 A 6/1986 Bunning et al.
4,599,206 A 7/1986 Billig et al.
4,668,651 A 5/1987 Billig et al.
4,717,775 A 1/1988 Billig et al.
4,769,498 A 9/1988 Billig et al.
4,774,361 A 9/1988 Maher et al.
4,835,299 A 5/1989 Maher et al.
4,885,401 A 12/1989 Billig et al.
5,059,710 A 10/1991 Abatjoglou et al.
5,102,505 A 4/1992 Sorensen
5,110,990 A 5/1992 Blessing et al.
5,113,022 A 5/1992 Abatjoblou et al.
5,114,473 A 5/1992 Abatjoglou et al.
5,179,055 A 1/1993 Wink et al.
5,183,943 A * 2/1993 Bryant et al. ............. 568/454
5,202,297 A 4/1993 Lorz et al.
5,235,113 A 8/1993 Sato et al.
5,254,741 A 10/1993 Lorz et al.
5,264,616 A 11/1993 Roeper et al.
5,277,532 A 1/1994 Pazzaglia
5,288,918 A * 2/1994 Maher .................. B01J 31/185
558/71
5,360,938 A 11/1994 Babin et al.
5,364,950 A 11/1994 Babin et al.
5,449,653 A 9/1995 Briggs et al.
5,491,266 A 2/1996 Babin et al.
5,710,344 A 1/1998 Breikss et al.
5,731,472 A 3/1998 Leung et al.
5,741,942 A * 4/1998 Bryant et al. ............. 568/454
5,741,945 A 4/1998 Bryant et al.
5,744,649 A 4/1998 Bryant et al.
5,763,671 A 6/1998 Bryant et al.
5,767,321 A 6/1998 Billig et al.
5,786,517 A 7/1998 Bryant et al.
5,874,640 A * 2/1999 Bryant .................. B01J 31/185
568/451
5,892,119 A 4/1999 Bryant et al.
6,090,987 A 7/2000 Billig et al.
6,153,800 A 11/2000 Gelling et al.
6,265,620 B1 7/2001 Urata et al.
6,294,700 B1 9/2001 Kanel et al.
6,312,996 B1 11/2001 Sogo
6,440,891 B1 8/2002 Maas et al.
7,009,068 B2 3/2006 Schmutzler et al.
(Continued)

FOREIGN PATENT DOCUMENTS

EP 0504814 A2 9/1992
EP 0590613 A2 4/1994
(Continued)

Primary Examiner — Yun Qian
(74) Attorney, Agent, or Firm — Quarles & Brady LLP

(57) ABSTRACT

The catalyst solution used in a hydroformylation process is prepared for storage by first reducing its acid concentration and/or water content, and then storing the solution under a blanket of syngas and/or an inert gas. Alternatively, or in addition to, the catalyst solution can be stored with an aqueous buffer comprising materials that will neutralize and/or absorb the acid species within the catalyst solution.

9 Claims, No Drawings

(56) References Cited

U.S. PATENT DOCUMENTS

| | | |
|---|---|---|
| 7,145,042 B2 | 12/2006 | Volland et al. |
| 7,196,230 B2 | 3/2007 | Peng et al. |
| 7,262,330 B2 | 8/2007 | Ueda et al. |
| 7,586,010 B2 | 9/2009 | Liu et al. |
| 7,615,645 B2 | 11/2009 | Volland et al. |
| 2003/0018220 A1 | 1/2003 | Packette et al. |
| 2009/0163742 A1 | 6/2009 | Mullin et al. |
| 2009/0171121 A1 | 7/2009 | Liu et al. |
| 2009/0299099 A1 | 12/2009 | Tolleson et al. |
| 2010/0010270 A1 | 1/2010 | Olivier-Bourbigon et al. |

FOREIGN PATENT DOCUMENTS

| | | |
|---|---|---|
| EP | 0675405 A2 | 10/1995 |
| WO | 97/20794 A1 | 6/1997 |
| WO | 2005/042458 A2 | 5/2005 |
| WO | 2008/071508 A1 | 6/2008 |
| WO | 2008/115740 A1 | 9/2008 |

\* cited by examiner

METHODS TO STORE TRANSITION METAL ORGANOPHOSPHOROUS LIGAND BASED CATALYSTS

CROSS REFERENCE TO RELATED APPLICATION

The present application is the national phase of PCT Patent Application No. PCT/US2012/033528 filed Apr. 13, 2012, which claims priority to U.S. Provisional Application No. 61/476,593, filed Apr. 18, 2011, the entire content of which is incorporated by reference herein.

BACKGROUND OF THE INVENTION

1. Field of the Invention

This invention relates to hydroformylation processes. In one aspect, the invention relates to hydroformylation processes that use transition metal bisphosphite-based catalysts while in another aspect, the invention relates to the shut down of such processes. In still another aspect, the invention relates to the storage and stabilization of the catalyst during such shut downs.

2. Description of the Related Art

Commercial hydroformylation processes must periodically be shut down for activities such as maintenance, inspection or, at times, when insufficient feed material is available or demand for product is down. During these periods of shutdown, the catalyst solution must be stored either in a part of, or in all of, the process equipment, or in one or more vessels external to the process equipment. One particular problem encountered during such shutdowns is that the catalyst, a transition metal, typically rhodium, in combination with one or more bisphosphite ligands must be stored and stabilized against de-activation. The bisphosphite ligands are expensive, and can decompose over time if not properly stored. This, of course, can lead to loss of catalyst activity and, under certain circumstances, even result in some precipitation of the metal. However, certain measures taken before and during storage of such catalyst solutions can reduce the decomposition of the bisphosphite ligands.

SUMMARY OF THE INVENTION

In one embodiment of the invention, the concentration of acid, particularly the aldehydes and phosphorus acids, in the catalyst solution is first reduced, neutralized or removed, and then the catalyst solution is stored under an atmosphere of syngas. The concentration of the acid can be reduced by any suitable method, e.g., extraction, base addition, precipitation, etc, and after storage the catalyst solution may again be treated to reduce the acid concentration prior to restarting the process.

In one embodiment of the invention, the concentration of acid, particularly the aldehyde-phosphonic and phosphorus acids, in the catalyst solution are first reduced, neutralized or removed, and then the catalyst solution is stored under an atmosphere of inert gas, e.g., nitrogen, methane, etc. This method is particularly useful in those situations in which an adequate amount of syngas is not available for any particular reason, e.g., in an unscheduled shut down due to a reactor upset.

In one embodiment of the invention, the catalyst solution is stored with materials present to either neutralize or absorb acidic species, in particular aldehydes and phosphorus acids, that are present in the catalyst solution either before storage or that are formed in the catalyst solution during storage. In one embodiment the catalyst solution is stored with a separate layer of aqueous buffer. In one embodiment the catalyst solution is stored with a base capable of neutralizing acids without decomposing the bisphosphite ligand. Once in storage with materials present to either neutralize or absorb acidic species, the catalyst solution is blanketed with an atmosphere of syngas or, if syngas is not available, then with an atmosphere of an inert gas. At the time the catalyst solution is brought out of storage for use in a hydroformylation process, the neutralization or absorption media can be removed by, for example, phase separation, precipitation or distillation.

DETAILED DESCRIPTION OF THE PREFERRED EMBODIMENT

Definitions

All references to the Periodic Table of the Elements refer to the Periodic Table of the Elements published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

All percentages, preferred amounts or measurements, ranges and endpoints are inclusive, that is, "up to 10" includes 10. "At least" is equivalent to "greater than or equal to," and "at most" is, thus, equivalent "to less than or equal to." Numbers are approximate unless otherwise specifically noted. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageous" is used to denote a degree of preference more than required, but less than is denoted by the term "preferably." Numerical ranges are provided within this disclosure for, among other things, the relative amount of reagents and process conditions.

Hydroformylation Process

The hydroformylation process, its reagents, conditions and equipment, are well known and described in, among other references, U.S. Pat. Nos. 4,169,861, 5,741,945, 6,153,800 and 7,615,645, EP 0590613 A2 and WO 2008/115740 A1. Typically, an olefinically unsaturated compound, e.g., propylene, is fed with synthesis gas, i.e., carbon monoxide (CO) and hydrogen ($H_2$), along with a three-component catalyst comprising a transition metal, preferably rhodium, and an organophosphorous ligand, preferably an organobisphosphite, and a suitable solvent, the contacting conducted at hydroformylation conditions into a multi-reactor system coupled in series, i.e., the output of the first reaction zone is fed as input to the subsequent reaction zone. The processing techniques can correspond to any of the known processing techniques employed in conventional hydroformylation processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion.

Olefinically-unsaturated compounds suitably employed are those capable of participating in a hydroformylation process to produce corresponding aldehyde product(s) and capable of being separated from the crude liquid hydroformylation product stream via vaporization. For the purposes of this disclosure, an "olefin" is defined as an aliphatic organic compound containing at least carbon and hydrogen atoms and having at least one carbon-carbon double bond (C=C). Preferably, the olefin contains one or two carbon-carbon double bonds, more preferably, one carbon-carbon double bond. The double bond(s) can be located at a terminal position along the carbon chain (alpha olefin) or at any internal position along the chain (internal olefin). Optionally, the olefin can comprise elements other than carbon and hydrogen including, for example, nitrogen, oxygen, and halogens, preferably, chlorine and bromine. The olefin can also be substituted with functional substituents including, for example, hydroxy, alkoxy, alkyl and cycloalkyl substituents. Preferably, the olefin comprises a substituted or unsubstituted olefin having a total of from 2 to 10 carbon atoms. Illustrative olefins include, without limitation, isomers of the following mono-olefins of butene, pentene, hexene, heptene, octene, nonene and decene, with specific non-limiting examples including 1-butene, 2-butene, 1-pentene, 2-pentene, and 1-hexene, 2-hexene, 3-hexene, and similarly, for heptene, octene, nonene, and decene. Other non-limiting examples of suitable olefins include ethylene, propylene, 2-methyl propene (isobutylene), 2-methylbutene, cyclohexene, butadiene, isoprene, 2-ethyl-1-hexene, styrene, 4-methyl styrene, 4-isopropyl styrene, 4-tert-butyl styrene, alpha-methyl styrene, 3-phenyl-1-propene, 1,4-hexadiene, 1,7-octadiene; as well as alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, 3-butenenitrile, 5-hexenamide, and dicyclopentadiene. The olefin can also be a mixture of olefins of similar or different molecular weights or structures (optionally with inerts such as the corresponding saturated alkanes).

Preferably, the olefin stream comprises a C4 raffinate I or C4 raffinate II isomeric mixture comprising butene-1, butene-2, isobutylene, butane, and optionally, butadiene. The C4 raffinate I stream comprises from 15 to 50 percent isobutylene and from 40 to 85 percent normal butenes, by weight, any remainder to 100 percent comprising primarily n-butane and isobutane. The normal butenes are generally a mixture of butene-1 and butene-2 (cis- and trans-forms). The relative proportion of components depend upon the composition of the petroleum feed, the conditions employed in steam cracking or catalytic cracking operation, and in the subsequent process steps, from which the C4 stream is derived. The C4 raffinate II stream comprises from 15 to 55 percent 1-butene, from 5 to 15 percent 2-butene (5 to 35 percent trans-2-butene), from 0.5 to 5 percent isobutylene, and from 1 to 40 percent butane, by volume. More preferably the olefin stream comprises propylene or mixtures of propylene and propane and other inerts.

Hydrogen and carbon monoxide are also required for the hydroformylation process. These gases can be obtained from any available source including petroleum cracking and refinery operations. Synthesis gas mixtures are preferably employed. The $H_2$:CO molar ratio of gaseous hydrogen to carbon monoxide can range, preferably, from 1:10 to 100:1, the more preferred $H_2$:CO molar ratio being from 1:10 to 10:1, and even more preferably, from 2:1 to 1:2. The gases are generally quantified by their partial pressures in the reactor based on their mole fraction in the gas phase (as measured by gas chromatography) and the total pressure using Dalton's Law. As used in the context of this disclosure, "syngas partial pressure" is the sum of the partial pressure of CO and the partial pressure of $H_2$.

Suitable metals that make up the transition metal-ligand complex catalyst include Group VIII metals selected from rhodium (Rh), cobalt (Co), iridium (Ir), ruthenium (Ru), iron (Fe), nickel (Ni), palladium (Pd), platinum (Pt), osmium (Os) and mixtures of two or more of these metals, with the preferred metals being rhodium, cobalt, iridium and ruthenium, more preferably rhodium, cobalt and ruthenium, and most preferably, rhodium. Other permissible metals include Group VIB metals selected from chromium (Cr), molybdenum (Mo), tungsten (W), and mixtures of two or more of these metals. Mixtures of metals from Groups VIB and VIII may also be used in this invention.

"Complex" and like terms means a coordination compound formed by the union of one or more electronically rich molecules or atoms (i.e., ligand) with one or more electronically poor molecules or atoms (e.g., transition metal). For example, the organophosphorous ligand used in the practice of this invention possesses at least one phosphorus (III) donor atom having one unshared pair of electrons, which is capable of forming a coordinate covalent bond with the metal. An organopolyphosphite ligand possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (in which each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefin, diolefin and triolefin, tetrahydrofuran, and the like.

The number of available coordination sites on the transition metal is well known in the art and depends upon the particular transition metal selected. The catalytic species may comprise a complex catalyst mixture in their monomeric, dimeric or higher nuclearity forms, which preferably are characterized by at least one organophosphorus-containing molecule complexed per one molecule of metal, for example, rhodium. For instance, the catalytic species of the preferred catalyst employed in the hydroformylation reaction may be complexed with carbon monoxide and hydrogen in addition to either the organopolyphosphite ligand or the organomonophosphite ligand.

The "organophosphorous ligands" in this invention comprise "hydrolysable phosphorous ligands" which are trivalent phosphorous ligands which contain at least one P—X* bond wherein X* is oxygen, nitrogen, chloride, fluoride or bromide. Examples include but are not limited to organophosphites (organomonophosphites or triorganomonophosphites), diorganophosphites (diorganomonophosphites), phosphino-phosphites, bisphosphites, organopolyphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—X* moieties such as polyphosphites, organopolyphosphites, polyphosphoramidites, etc. and mixed P—X* moieties such as phosphite-phosphoramidites, fluorophosphite-phosphites, and the like. Illustrative metal-organophosphorous ligand complex catalyzed hydroformylation processes which may experience such hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. Likewise other P—X* containing species that will likely under under-go similar hydrolytic degradation include organophosphonites, phosphoramidites, fluorophosphonites, and the like such as described in U.S. Pat. No. 7,009,068, WO 2008/071508 U.S. Pat. No. 5,710,344, WO 2005/042458, U.S. Pat. Nos. 7,145, 042, 6,440,891, 7,586,010, US Published Patent Applications 2009/0171121 and 2009/0299099, and U.S. Pat. No. 6,265,620.

The preferred organopolyphosphite ligand broadly comprises a plurality of phosphite groups, each of which contains one trivalent phosphorus atom bonded to three hydrocarbyloxy radicals. Hydrocarbyloxy radicals that link and bridge two phosphite groups are more properly referred to as "divalent hydrocarbyldioxy radicals." These bridging diradicals are not limited to any particular hydrocarbyl species. On the other hand, hydrocarbyloxy radicals that are pendant from a phosphorus atom and not bridging two phosphite groups (i.e., terminal, non-bridging), are each required to consist essentially of an aryloxy radical. "Aryloxy" broadly refers to either of two types of aryloxy radicals: (1) a monovalent aryl radical bonded to a single ether linkage, as in —O-aryl, wherein the aryl group comprises a single aromatic ring or multiple aromatic rings that are fused together, directly linked, or indirectly linked (such that different aromatic groups are bound to a common group such as a methylene or ethylene moiety), or (2) a divalent arylene radical bonded to two ether linkages, as in —O-arylene-O— or —O-arylene-arylene-O—, in which the arylene group comprises a divalent hydrocarbon radical having a single aromatic ring or multiple aromatic rings that are fused together, directly linked, or indirectly linked (such that the different aromatic groups are bound to a common group such as a methylene or ethylene moiety). Preferred aryloxy groups contain one aromatic ring or from 2 to 4 fused or linked aromatic rings, having from about 5 to about 20 carbon atoms, for example, phenoxy, naphthyloxy, or biphenoxy, as well as arylenedioxy radicals, such as, phenylenedioxy, naphthylenedioxy, and biphenylenedioxy. Any of these radicals and groups may be unsubstituted or substituted.

Preferred organopolyphosphite ligands comprise two, three or higher numbers of phosphite groups. Mixtures of such ligands may be employed if desired. Achiral organopolyphosphites are preferred. Representative organopolyphosphites include those of formula (I):

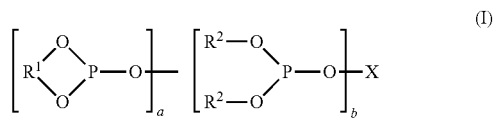

in which X represents a substituted or unsubstituted n-valent organic bridging radical containing from 2 to 40 carbon atoms, each $R^1$ is the same or different and represents a divalent arylene radical containing from 6 to 40 carbon atoms, preferably, from 6 to 20 carbon atoms; each $R^2$ is the same or different and represents a substituted or unsubstituted monovalent aryl radical containing from 6 to 24 carbon atoms; a and b can be the same or different and each has a value of 0 to 6, with the proviso that the sum of a+b is 2 to 6 and n equals a+b. When a has a value of 2 or more, each $R^1$ radical may be the same or different, and when b has a value of 1 or more, each $R^2$ radical may be the same or different.

Representative n-valent (preferably divalent) hydrocarbon bridging radicals represented by X include both acyclic radicals and aromatic radicals, such as alkylene, alkylene-Qm-alkylene, cycloalkylene, arylene, bisarylene, arylene-alkylene, and arylene-$(CH_2)_y$-Q-$(CH_2)_y$— arylene radicals, wherein each y is the same or different and is a value of 0 or 1. Q represents a divalent bridging group selected from —C($R^3$)$_2$—, —O—, —S—, —$NR^4$—, —Si($R^5$)$_2$— and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, for example, an alkyl radical having 1 to 4 carbon atoms; each $R^5$ is the same or different and represents hydrogen or an alkyl radical, preferably, a $C_{1-10}$ alkyl radical, and m is a value of 0 or 1. The more preferred acyclic radicals represented by X above are divalent alkylene radicals while the more preferred aromatic radicals represented by X are divalent arylene and bisarylene radicals, such as disclosed more fully, for example, in U.S. Pat. Nos. 4,769,498; 4,774,361; 4,885,401; 5,179,055; 5,113, 022; 5,202,297; 5,235,113; 5,264,616; 5,364,950; 5,874, 640; 5,892,119; 6,090,987; and 6,294,700.

Illustrative preferred organopolyphosphites include bisphosphites such as those of formulae (II) to (IV):

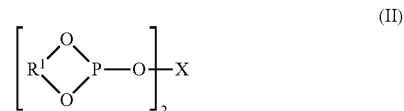

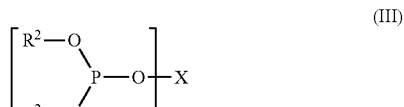

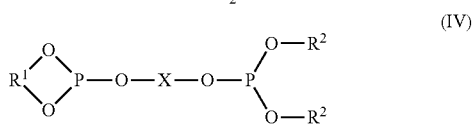

in which $R^1$, $R^2$ and X of formulae (II) to (IV) are the same as defined above for formula (I). Preferably X represents a divalent hydrocarbon radical selected from alkylene, arylene, arylene-alkylene-arylene, and bisarylene; $R^1$ represents a divalent hydrocarbon radical selected from arylene, arylene-alkylene-arylene, and bisarylene; and each $R^2$ radical represents a monovalent aryl radical. Organopolyphosphite ligands of such formulae (II) to (IV) may be found disclosed, for example, in U.S. Pat. Nos. 4,668,651; 4,748, 261; 4,769,498; 4,774,361; 4,885,401; 5,113,022; 5,179, 055; 5,202,297; 5,235,113; 5,254,741; 5,264,616; 5,312,996 and 5,364,950.

Representative of more preferred classes of organobisphosphites are those of the formulae (V) to (VII).

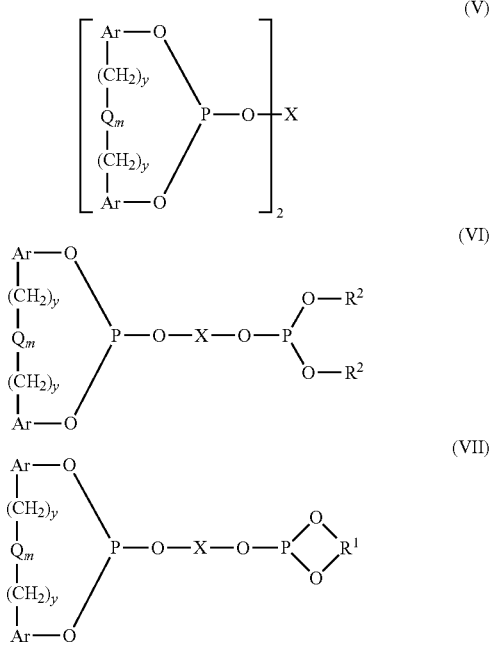

in which Q, $R^1$, $R^2$, X, m, and y are as defined above, and each Ar is the same or different and represents a substituted or unsubstituted divalent aryl radical. Most preferably, X represents a divalent aryl-$(CH_2)_y$-$(Q)_m$-$(CH_2)_y$— aryl radical wherein each y individually has a value of 0 or 1; m has a value of 0 or 1 and Q is —O—, —S— or —$C(R^3)_2$ where each $R^3$ is the same or different and represents hydrogen or a $C_{1-10}$ alkyl radical, preferably, methyl. More preferably, each aryl radical of the above-defined Ar, X, $R^1$ and $R^2$ groups of formulae (V) to (VII) may contain 6 to 18 carbon atoms and the radicals may be the same or different, while the preferred alkylene radicals of X may contain 2 to 18 carbon atoms. In addition, preferably the divalent Ar radicals and divalent aryl radicals of X of the above formulae are phenylene radicals in which the bridging group represented by —$(CH_2)_y$-$(Q)_m$-$(CH_2)_y$— is bonded to the phenylene radicals in positions that are ortho to the oxygen atoms of the formulae that connect the phenylene radicals to their phosphorus atom. Any substituent radical when present on such phenylene radicals is preferably bonded in the para and/or ortho position of the phenylene radicals in relation to the oxygen atom that bonds the given substituted phenylene radical to its phosphorus atom.

Moreover, if desired any given organopolyphosphite in the above formulae (I) to (VII) may be an ionic phosphite, that is, may contain one or more ionic moieties selected from the group consisting of: —$SO_3M$, wherein M represents an inorganic or organic cation, —$PO_3M$ wherein M represents an inorganic or organic cation, —$N(R^6)3X^1$, wherein each $R^6$ is the same or different and represents a hydrocarbon radical containing from 1 to 30 carbon atoms, for example, alkyl, aryl, alkaryl, aralkyl, and cycloalkyl radicals, and $X^1$ represents inorganic or organic anion, —$CO_2M$ wherein M represents inorganic or organic cation, as described, for example, in U.S. Pat. Nos. 5,059,710; 5,113,022; 5,114,473 and 5,449,653. Thus, if desired, such organopolyphosphite ligands may contain from 1 to 3 such ionic moieties; however, preferably only one such ionic moiety is substituted on any given aryl moiety when the organopolyphosphite ligand contains more than one such ionic moiety. Suitable cationic species of M include, without limitation, hydrogen (i.e., a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anions $X^1$ include, for example, sulfate, carbonate, phosphate, chloride, acetate, oxalate and the like.

Of course any of the $R^1$, $R^2$, X, Q and Ar radicals of such non-ionic and ionic organopolyphosphites of formulae (I) to (VII) above may be substituted if desired, with any suitable substituent, optionally containing from 1 to 30 carbon atoms, that does not adversely affect the desired result of the process of this invention. Substituents that may be on the radicals in addition, of course, to corresponding hydrocarbon radicals such as alkyl, aryl, aralkyl, alkaryl and cyclohexyl substituents, may include for example silyl radicals such as —$Si(R^7)_3$; amino radicals such as —$N(R^7)_2$; phosphine radicals such as -aryl-$P(R^7)_2$; acyl radicals such as —$C(O)R^7$; acyloxy radicals such as —$OC(O)R^7$; amido radicals such as —$CON(R^7)_2$ and —$N(R^7)COR^7$; sulfonyl radicals such as —$SO_2R^7$, alkoxy radicals such as —$OR^7$; sulfinyl radicals such as —$SOR^7$; sulfenyl radicals such as —$SR^7$; phosphonyl radicals such as —$P(O)(R^7)_2$; as well as halogen, nitro, cyano, trifluoromethyl, hydroxy radicals, and the like, wherein preferably each $R^7$ radical individually represents the same or different monovalent hydrocarbon radical having from 1 to about 18 carbon atoms (for example, alkyl, aryl, aralkyl, alkaryl and cyclohexyl radicals) with the proviso that in amino substituents such as —$N(R^7)_2$ each $R^7$ taken together can also represent a divalent bridging group that forms a heterocyclic radical with the nitrogen atom, and in amido substituents such as —$C(O)N(R^7)_2$ and —$N(R^7)COR^7$ each $R^7$ bonded to N can also be hydrogen. Of course any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl and naphthyl; aralkyl radicals such as benzyl, phenylethyl, and triphenylmethyl; alkaryl radicals such as tolyl and xylyl; alicyclic radicals such as cyclopentyl, cyclohexyl, 1-methylcyclohexyl, cyclo-octyl, and cyclohexylethyl; alkoxy radicals such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals such as phenoxy; as well as silyl radicals such as —$Si(CH_3)_3$, —$Si(OCH_3)_3$, and —$Si(C_3H_7)_3$; amino radicals such as —$NH_2$, —$N(CH_3)_2$, —NHCH$_3$, and —NH(C$_2$H$_5$); arylphosphine radicals such as —P(C$_6$H$_5$)$_2$; acyl radicals such as —C(O)CH$_3$, —C(O)C$_2$H$_5$, and —C(O)C$_6$H$_5$; carbonyloxy radicals such as —C(O)OCH$_3$; oxycarbonyl radicals such as —O(CO)C$_6$H$_5$; amido radicals such as —CONH$_2$, —CON(CH$_3$)$_2$, and —NHC(O)CH$_3$; sulfonyl radicals such as —S(O)$_2$C$_2$H$_5$; sulfinyl radicals such as —S(O)CH$_3$; sulfenyl radicals such as —SCH$_3$, —SC$_2$H$_5$, and —SC$_6$H$_5$; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), and —P(O)(H)(C$_6$H$_5$).

Specific examples of organobisphosphites are Ligands A-S of WO 2008/115740.

The organomonophosphites include any organic compound comprising one phosphite group. A mixture of organomonophosphites can also be used. Representative organomonophosphites include those of formula (VIII).

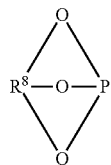
(VIII)

in which R$^8$ represents a substituted or unsubstituted trivalent hydrocarbon radical containing 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycyclohexane. Such organomonophosphites may be found described in greater detail, for example, in U.S. Pat. No. 4,567,306.

Representative diorganophosphites include those of formula (IX).

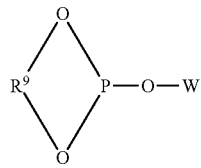
(IX)

in which R$^9$ represents a substituted or unsubstituted divalent hydrocarbon radical containing 4 to 40 carbon atoms or greater and W represents a substituted or unsubstituted monovalent hydrocarbon radical containing 1 to 18 carbon atoms.

Representative substituted and unsubstituted monovalent hydrocarbon radicals represented by W in formula IX include alkyl and aryl radicals, while representative substituted and unsubstituted divalent hydrocarbon radicals represented by R$^9$ include divalent acyclic radicals and divalent aromatic radicals. Illustrative divalent acyclic radicals include, for example, alkylene, alkylene-oxy-alkylene, alkylene-NX$^2$-alkylene, wherein X$^2$ is hydrogen or a substituted or unsubstituted hydrocarbon radical, alkylene-S-alkylene, and cycloalkylene radicals. The more preferred divalent acyclic radicals are the divalent alkylene radicals, such as disclosed more fully, for example, in U.S. Pat. Nos. 3,415,906 and 4,567,302. Illustrative divalent aromatic radicals include, for example, arylene bisarylene, arylene-alkylene, arylene-alkylene-arylene, arylene-oxy-arylene, arylene-NX$^2$-arylene, wherein X$^2$ is as defined above, arylene-S-arylene, and arylene-S-alkylene. More preferably, R$^9$ is a divalent aromatic radical, such as disclosed more fully, for example, in U.S. Pat. Nos. 4,599,206 and 4,717,775.

Representative of a more preferred class of diorganomonophosphites are those of formula (X).

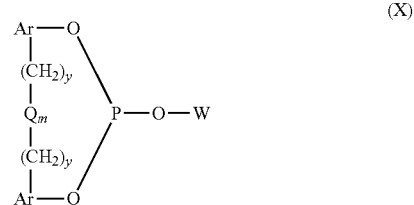
(X)

in which W is as defined above, each Ar is the same or different and represents a substituted or unsubstituted divalent aryl radical, each y is the same or different and is value of 0 or 1, Q represents a divalent bridging group selected from —C(R$^{10}$)$_2$—, —O—, —S—, —NR$^{11}$—, —Si(R$^{12}$)$_2$— and —CO—, in which each R$^{10}$ is the same or different and represents hydrogen, alkyl radicals having from 1 to 12 carbon atoms, phenyl, tolyl, and anisyl, R$^{11}$ represents hydrogen or an alkyl radical of from 1 to 10 carbon atoms, preferably, methyl, each R$^{12}$ is the same or different and represents hydrogen or an alkyl radical having 1 to 10 carbon atoms, preferably, methyl, and m is a value of 0 or 1. Such diorganomonophosphites are described in greater detail, for example, in U.S. Pat. Nos. 4,599,206, 4,717,775 and 4,835,299.

Representative triorganomonophosphites include those of formula (XI).

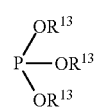
(XI)

in which each R$^{13}$ is the same or different and is a substituted or unsubstituted monovalent hydrocarbon radical, for example, an alkyl, cycloalkyl, aryl, alkaryl, or aralkyl radical, which may contain from 1 to 24 carbon atoms. Illustrative triorganomonophosphites include, for example, trialkylphosphites, dialkylarylphosphites, alkyldiarylphosphites, and triarylphosphites, such as, triphenylphosphite, tris(2,6-triisopropyl)phosphite, tris(2,6-di-tert-butyl-4-methoxyphenyl)phosphite, as well as the more preferred tris(2,4-di-tert-butylphenyl)phosphite. The monovalent hydrocarbon radical moieties themselves may be functionalized with the proviso that the functional groups do not significantly interact with the transition metal or otherwise inhibit hydroformylation. Representative functional groups include alkyl or aryl radicals, ethers, nitriles, amides, esters, —N(R$^{11}$)$_2$, —Si(R$^{12}$)$_3$, phosphates, and the like, in which R$^{11}$ and R$^{12}$ are as previously defined. Such triorganomonophosphites are described in more detail in U.S. Pat. Nos. 3,527,809 and 5,277,532.

As a further option any organomonophosphite-monophosphate ligand or organomonophosphite-polyphosphate ligand may be employed as the organomonophosphite ligand. For example, any of the organopolyphosphite ligands, including preferred organobisphosphite ligands as previously described, may be subjected to oxidation such that all but one of the phosphorus (III) atoms is converted into phosphorus (V) atoms. The resulting oxidized ligand can comprise an organomonophosphite-polyphosphate or, preferably, an organomonophosphite-monophosphate, which suitably is employed in a 2/1 molar excess relative to the transition metal. As here used "organomonophosphite ligand" and like terms include organomonophosphite-monophosphate ligand and organomonophosphite-polyphosphate ligand (as appropriate to the text in which the term is used) unless specifically noted otherwise.

As a further option any organomonophosphoramidite ligand can be used as, or in combination with any other organophosphorous ligand, and any organopolyphosphoramidite ligand can be used as, or in combination with any other organophosphorous ligand. Organophosphoramidite ligands are known, and they are used in the same manner as organophosphite ligands. Representative organophosphoramidite ligands are of formulae (XII-XIV).

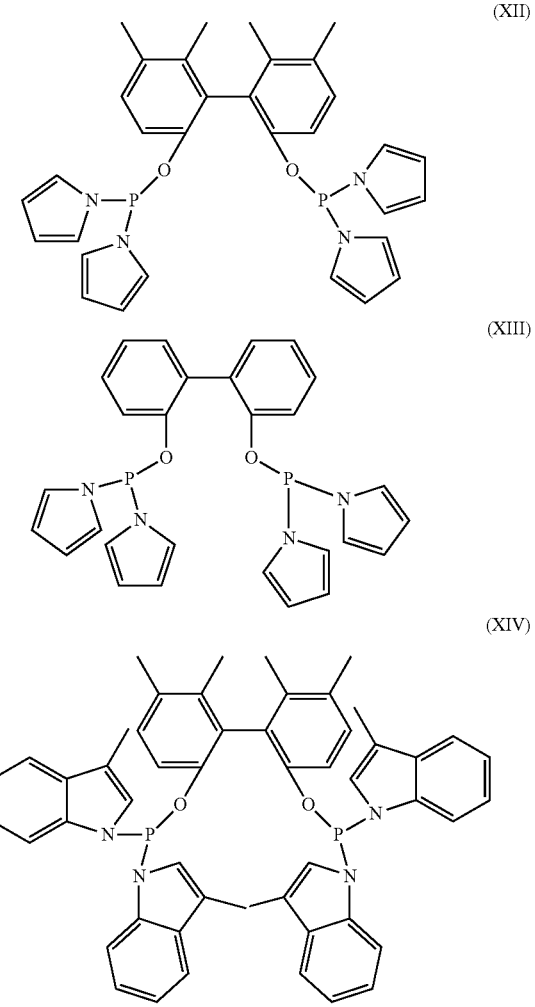

Organophosphoramidites are further described in, for example, U.S. Pat. No. 7,615,645. As here used "organophosphorous ligands" and like terms include organomonophosphoramidite and organopolyphosphoramidite ligands unless specifically noted otherwise.

The hydroformylation catalyst comprises a stabilized complex of (A) transition metal (e.g., rhodium typically supplied as a rhodium catalyst precursor such as $Rh(CO)_2$ (Acac)), (B) organophosphorous ligand, and (C) excess (free) organophosphorous ligand which is provided in excess molar quantity with respect to the rhodium metal component of the stabilized catalyst complex.

The catalyst can be prepared in situ in a hydroformylation reaction zone or, alternatively, it can be prepared ex-situ and subsequently introduced into the reaction zone with the appropriate hydroformylation reactants. In one embodiment the catalyst is prepared by admixing one mole of suitable transition metal source with 1 mole to 5-100 moles of organophosphorous ligand. In one embodiment the catalyst is prepared by admixing at a ratio of one mole of a suitable rhodium source to 5-100 moles of the organophosphorous ligand and after initiation of the hydroformylation reaction, the polydentate ligand is added.

The catalytic species may comprise a complex catalyst mixture in its monomeric, dimeric or higher nuclearity forms which preferably are characterized by at least one organophosphorus-containing molecule complexed per one molecule of transition metal. For instance, the transition metal may be complexed with carbon monoxide and hydrogen in addition to either a monodentate phosphite ligand or a polydentate ligand.

The catalyst and its preparation are more fully described in U.S. Pat. Nos. 4,169,861, 5,741,945, 6,153,800 and 7,615,645, and WO 2008/115740.

The hydroformylation catalysts may be in homogeneous or heterogeneous form during the reaction and/or during the product separation. The amount of metal-ligand complex catalyst present in the reaction medium need only be that minimum amount necessary to catalyze the process. If the transition metal is rhodium, then concentrations in the range of 10 to 1000 parts per million (ppm), calculated as free rhodium, in the hydroformylation reaction medium is sufficient for most processes, while it is generally preferred to employ from 10 to 500 ppm rhodium, and more preferably from 25 to 350 ppm rhodium.

In addition to the metal-ligand complex catalyst, free ligand (i.e., ligand that is not complexed with the metal) may also be present in the hydroformylation reaction medium. The free ligand, mono- or polydentate, is preferably, but not necessarily, the same as the ligand of the metal-ligand complex catalyst employed. The hydroformylation process of this invention may involve from 0.1 moles or less to 100 moles or higher, of free ligand per mole of metal in the hydroformylation reaction medium. Preferably the hydroformylation process is carried out in the presence of from 1 to 50 moles of ligand, and more preferably from 1.1 to 4 moles of ligand, per mole of metal present in the reaction medium; the amounts of ligand being the sum of both the amount of ligand that is bound (complexed) to the metal present and the amount of free (non-complexed) ligand present. Of course, if desired, make-up or additional ligand can be supplied to the reaction medium of the hydroformylation process at any time and in any suitable manner, e.g. to maintain a predetermined level of free ligand in the reaction medium.

As a general procedure, the catalyst system is first formed in a deoxygenated solvent medium in a hydroformylation reaction zone. Excess ligand can perform as the solvent medium. The first hydroformylation zone is pressured with hydrogen and carbon monoxide and heated to a selected reaction temperature. The olefinically unsaturated compound is fed to the first hydroformylation zone, and the reaction is conducted until the desired conversion yield and efficiency have been attained at which time the product of the first reaction zone is transferred to the subsequent reaction zone(s) in which fresh and/or recycled reagents are added. The reaction in this subsequent reaction zone(s) continues until the desired conversion yield and efficiency are attained at which time the product of the last reaction zone is recovered and purified. In a continuous system the catalyst is preferably recycled back to the first reaction zone.

The reaction conditions of the hydroformylation process can vary widely. For instance, the $H_2$:CO molar ratio of gaseous hydrogen to carbon monoxide advantageously can range from 1:10 to 100:1 or higher, the more preferred hydrogen to carbon monoxide molar ratio being from 1:10 to 10:1. Advantageously, the hydroformylation process can be conducted at a reaction temperature greater than −25° C., more preferably, greater than 50° C. The hydroformylation process advantageously can be conducted at a reaction temperature less than 200° C., preferably, less than 120° C. Advantageously, the total gas pressure comprising olefinic reactant, carbon monoxide, hydrogen, and any inert lights can range from 1 psia (6.9 kPa) to 10,000 psia (68.9 MPa). Preferably, the process be operated at a total gas pressure comprising olefinic reactant, carbon monoxide, and hydrogen of less than 2,000 psia (13,800 kPa), and more preferably, less than 500 psia (3450 kPa). Advantageously, the carbon monoxide partial pressure varies from 1 psia (6.9 kPa) to 1000 psia (6,900 kPa), and preferably from 3 psia (20.7 kPa) to 800 psia (5,516 kPa), and more preferably, from 15 psia (103.4 kPa) to 100 psia (689 kPa); while the hydrogen partial pressure varies preferably from 5 psia (34.5 kPa) to 500 psia (3,450 kPa), and more preferably from 10 psia (69 kPa) to 300 psia (2,070 kPa).

The feed flow rate of synthesis gas (CO+$H_2$) can vary widely over any operable flow rate sufficient to obtain the desired hydroformylation process. The syngas feed flow rate depends upon the specific form of catalyst, olefin feed flow rate, and other operating conditions. Likewise, the vent flow rate from the Oxo reactor(s) can be any operable flow rate sufficient to obtain the desired hydroformylation process. Vent flow rate is dependent upon the scale of the reactor and the purity of the reactant and syngas feeds. Suitable syngas feed flow rates and vent flow rates are well known or easily calculated by those skilled in the art. In one embodiment the $H_2$ and CO partial pressures are controlled such that the reaction is conducted under conditions in which the hydroformylation rate is positive order for syngas ($H_2$ and CO) partial pressures for the monophosphite catalyst and negative order for the CO partial pressure for the bisphosphite catalysts (such as described in WO 2008/115740 A1).

Inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including o-dichlorobenzene; ethers such as tetrahydrofuran, dimethoxyethane and dioxane; halogenated paraffins including methylene chloride; esters (e.g., ethyl acetate, di-2-ethyl hexyl phthalate, 2,2,4-trimethyl-1,3-pentanediol monoisobutyrate), paraffinic hydrocarbons such as heptane; and the like. The preferred solvent is the aldehyde product and/or the oligomers of the aldehyde product along with the reactive olefin or olefins.

In one embodiment the hydroformylation process is carried out in a multi-staged reactor such as described in U.S. Pat. No. 5,763,671. Such multi-staged reactors can be designed with internal, physical barriers that create more than one theoretical reactive stage or zone per vessel. The effect is like having a number of reactors inside a single continuous stirred tank reactor vessel. Multiple reactive stages within a single vessel are a cost effective way of using the reactor vessel volume. It significantly reduces the number of vessels that otherwise are required to achieve the same results. Obviously, however, if the goal is to have different partial pressures of a reactant in different stages of the process, then two or more reactors or vessels are employed. Reaction zones can be in parallel or series but most preferably are in series.

The hydroformylation process of this invention is typically conducted in a two-stage, continuous manner. Such processes are well known in the art and may involve: (a) hydroformylating the olefinic starting material(s) with carbon monoxide and hydrogen in a liquid homogeneous reaction mixture comprising a solvent, the metal organophosphorous ligand complex catalyst, free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode in which a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed in U.S. Pat. No. 4,148,830 or a gas recycle procedure such as disclose in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990. With multiple reactor vessels, they can be run in series or in parallel (for mixtures of both schemes).

As used in the context of this invention, "catalyst solution" is any solution where the catalytic metal (e.g., rhodium) and/or organophosphorous ligand are present and will be used in the process to manufacture aldehydes. This includes reactor contents (generally referred to as the "reaction zone" including heat exchangers), catalyst-product separation zone (typically a vaporizer or decanter), any catalyst treatment zone (typically an extractor, filter, knock-out pots, etc.), and any piping, heat exchangers, and/or pumps connecting any of the above. The catalyst solution comprises metal-organophosphorous complex, free (uncomplexed) ligand, unreacted reagents (typically olefin and syngas), products, by-products (e.g., alcohols), ligand degradation products, and a suitable solvent (typically aldehyde heavies as described in U.S. Pat. No. 4,148,830).

At the time of a shut down of a hydroformylation process, the catalyst may be in a variety of states which may impact the storage stability of the catalyst. For example, the catalyst solution may contain high or low levels of acids and/or high or low levels of water. Since the hydrolysis of the organophosphorous ligand is dependant on the water content and the presence of acid catalysts, the water and/or acid level is reduced as much as possible. However, it is not always possible to achieve both low acid and low water content, especially during unplanned shutdowns. The present invention avoids storing the catalyst solution with both high acid and high water content (in the absence of buffering).

In one embodiment of the invention, at the time of a shut down of a hydroformylation process the concentration of acid, particularly the aldehyde-phosphonic and phosphorus acids, in the catalyst solution is first reduced, neutralized or removed, and then the catalyst solution is stored under an atmosphere of syngas. For example, as described in U.S. Pat. Nos. 4,599,206, 5,288,918, 5,741,942, 5,741,942, 4,835,299 and US 2003/0018220, reactions with water, adventitious oxygen, and/or aldehyde generate acids such as 1-hydroxybutylphosphonic acid (an aldehyde-phosphonic acid derived from butyraldehyde), phosphorous acid ($H_3PO_3$), phosphoric acid ($H_3PO_4$), ligand degradation acids such as ArO—P(=O)H(OH) and ArO—P(=O)(OH)$_2$, and hydrofluoric acid (HF). Oxidation of the aldehyde product by adventitious oxygen or peroxides will yield the corresponding carboxylic acid. The presence and concentration of these acid impurities can be measured in the catalyst solution directly ($^{31}$P NMR, IC) or by water extraction prior to analysis (IC, titration) or indirectly by measuring the acid components in an extractor aqueous effluent ($^{31}$P NMR, IC). All of the acid measurements are typically converted to "$H_3PO_3$ equivalents" for comparison purposes. The concentration of the acid can be reduced by any suitable method, e.g., extraction, base addition, precipitation, etc., such as those described in the preceding patent documents. The acid content should be reduced to less than (<) 1000 parts per million (ppm) (as $H_3PO_3$), preferably <800 ppm (as $H_3PO_3$), preferably <600 ppm (as $H_3PO_3$), preferably <400 ppm (as $H_3PO_3$), preferably <200 ppm (as $H_3PO_3$), preferably <100 ppm (as $H_3PO_3$), preferably <50 ppm (as $H_3PO_3$), preferably <20 ppm (as $H_3PO_3$), and most preferably <10 ppm (as $H_3PO_3$) in the catalyst solution.

In one embodiment of the invention, the amount of water in the catalyst solution is also reduced before storage. The water is normally desirable to hydrolyze the poisoning phosphite complex during commercial operation (U.S. Pat. No. 5,288,918) but may not be desirable during storage. To minimize hydrolysis and the formation of acids, the water content is reduced as much as possible but complete removal of the water is not practical. The water content of the catalyst solution can be reduced by any convenient method, e.g., evaporation, extraction, etc., and it can be reduced before, during or after the reduction in the acid concentration of the catalyst solution. One example is given in U.S. Pat. No. 7,262,330 but a simpler process is to use an existing vaporizer to remove the water with the product and shut off any water source (e.g., by-passing an aqueous extractor). The water content in storage is typically less than (<) 5 weight percent (wt %), preferably <4 wt %, preferably <3 wt %, preferably <2 wt %, preferably <1 wt %, preferably <0.8 wt %, preferably <0.5 wt %, preferably <0.25 wt %, and most preferably less than 0.1 wt % (as measured by NIR or Karl-Fischer titration).

In one embodiment of the invention, both the acid concentration and water content of the catalyst solution are reduced before the catalyst solution is stored.

The desired water and acid levels reported here are those levels in the average catalyst solution recognizing that the concentrations may vary throughout the process (e.g., the reactor contents may be higher than the vaporizer tails simply by dilution).

Once the acid concentration and/or water content of the catalyst solution is reduced to the desired level(s), the catalyst solution is stored under a blanket of syngas. The catalyst solution of reduced acid concentration and/or water content can be stored within or outside of the hydroformylation equipment. Whether stored within or without the equipment, it can either be continuously or periodically circulated, or it can lie quiescent. If stored outside of the hydroformylation process equipment, it is typically transferred by pump from the hydroformylation process equipment or the equipment used to reduce the acid concentration and/or water content to a holding vessel made of a material that is essentially inert to the catalyst solution, e.g., the same material of which the hydroformylation equipment is constructed. The syngas is used in an amount and in a manner sufficient to blanket the stored catalyst solution and protect the solution from compounds reactive with the catalyst or its component parts. Typically, the minimum amount of syngas used is that necessary to insure that the solution is at least under atmospheric pressure and that the CO and $H_2$ partial pressure (pp) is at least 5 pounds per square inch (psi) each for a total syngas pressure of at least 10 psi.

At the time of a shut down of a hydroformylation process, in one embodiment of the invention the catalyst solution is stored with materials that will neutralize and/or absorb acidic species, in particular aldehyde and phosphoric acids, that are either present at the time of storage, or are formed during storage. This situation may arise when it was not possible to reduce the contained water from the catalyst solution prior to storage such as during an unplanned shutdown or due to vaporizer maintenance. In this case, the prevention of the buildup of acidic impurities and the avoidance of the onset of the autocatalytic hydrolysis is desired, and it is obtained by removing the acid catalyst. The neutralization and/or absorption materials are typically provided as part of an aqueous buffer solution or mixture at a concentration sufficient to neutralize or absorb at least 50, typically at least 90 and more typically at least 95, percent of the acidic species within the catalyst solution. Preferably, the concentration of the materials in the buffer solution or mixture is sufficient to neutralize and/or absorb all of the acidic species present within the catalyst solution at the time of storage and that may form over the period of storage. This can be effected by adding reagents to the stored catalyst to absorb the acids during storage. As an example, adding a buffer solution comprising a substituted amine or an epoxide to the catalyst solution in the storage tank to react with, absorb, or otherwise neutralize the acid as it is formed. These can be the same or different acid removal technologies employed prior to shutdown.

If a buffer solution is used, it may be added to the stored catalyst solution, or, preferably, it may be mixed with the catalyst solution to form a two phase mixture that will separate over time. In one embodiment the buffer solution is mixed, either continuously or intermittently, with the stored catalyst solution over the entire period of storage. The mixing can be effected by any means, e.g., use of a mechanical stirring device such as a propeller, a pump, etc. Like the stored catalyst solution with reduced acid concentration, the catalyst solution in this embodiment can also have a reduced water content, and is stored under a blanket of syngas and/or inert gas.

In one embodiment of the invention, the syngas is used neat to blanket the stored catalyst solution. In one embodiment of the invention, the syngas is used in combination with one or more inert gases, e.g., nitrogen, helium, methane, etc., to blanket the stored catalyst solution. In one embodiment of the invention, syngas is not used in the blanketing of the stored catalyst solution; rather the catalyst solution is stored under a blanket of an inert gas.

The neutralization and/or absorption media can be removed from the catalyst solution by any convenient means, e.g., separation, precipitation or distillation, at the time the catalyst solution is ready to be removed from storage and placed back into operation within the hydroformylation process. This can be most conveniently done by passing the stored catalyst solution through the extractor which will remove any aqueous layer or buffer.

In one embodiment of the invention the acid concentration and water content of the catalyst solution is reduced before storage, and then the catalyst solution is stored with materials that will neutralize and/or absorb acidic species and under a blanket of syngas and/or an inert gas.

In one embodiment the acid concentration of the stored catalyst solution is reduced prior to restart of the hydroformylation process by circulating the catalyst solution through an aqueous extractor, where the temperature of the catalyst solution is below the normal temperature employed in the reactor, typically less than 50° C. Optionally the vaporizer may be initiated prior to starting the reactor olefin feeds to remove some of the water. In either case, it is preferred that the reactors maintain a positive syngas pressure, e.g., greater than (>) 10 psi.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A method of preparing a hydroformylation catalyst solution for storage, the catalyst solution comprising:

A. a transition metal in combination with one or more bisphosphite ligands,
    B. a concentration of acidic species, and
    C. water, the method comprising the steps of (i) mixing the catalyst solution with an aqueous buffer solution comprising one or more materials that will neutralize and/or absorb at least 50 percent of the acidic species and (ii) storing the mixed catalyst solution and aqueous buffer solution under a blanket of syngas.

2. The method of claim 1 in which the aqueous buffer solution comprises at least one of a substituted amine or an epoxide.

3. The method of claim 1 in which the catalyst solution is stored with the aqueous buffer solution as a separate phase in contact with the catalyst solution.

4. The method of claim 1 in which the catalyst solution and aqueous buffer solution are stored in a mixed and agitated state.

5. The method of claim 1 in which the catalyst solution and the aqueous buffer solution are stored under a blanket of syngas in combination with one or more inert gases.

6. The method of claim 1 in which the catalyst solution and the aqueous buffer solution are stored within equipment of the hydroformylation process.

7. The method of claim 1 in which the catalyst solution and the aqueous buffer solution are stored outside of the equipment of the hydroformylation process.

8. The method of claim 1 in which the transition metal of the hydroformylation catalyst is rhodium.

9. The method of claim 1 further comprising the step of shutting down a hydroformylation process.

* * * * *